(12) United States Patent
Jacobsen et al.

(10) Patent No.: US 6,398,758 B1
(45) Date of Patent: Jun. 4, 2002

(54) MEDICAMENT DELIVERY SYSTEM

(76) Inventors: Stephen C. Jacobsen, 274 S. 1200 East, Salt Lake City, UT (US) 84102; Clark Davis, 4564 Wallace La., Salt Lake City, UT (US) 84117

(\*) Notice: Subject to any disclaimer, the term of this patent is extended or adjusted under 35 U.S.C. 154(b) by 0 days.

(21) Appl. No.: 09/250,736

(22) Filed: Feb. 16, 1999

(51) Int. Cl.[7] .................. A61M 29/00; A61M 31/00; A61F 11/00
(52) U.S. Cl. ............... 604/104; 604/285; 604/11; 606/108
(58) Field of Search .............. 604/890.1, 891.1, 604/11–13, 15, 18, 104, 285–287; 623/1.11, 1.12, 1.2, 1.32, 1.33, 1.42, 1.43; 606/108, 109

(56) References Cited

U.S. PATENT DOCUMENTS

| | | | |
|---|---|---|---|
| 3,796,217 A | \* | 3/1974 | Arlen ..................... 128/260 |
| 3,815,601 A | \* | 6/1974 | Schaefer .................. 128/285 |
| 4,286,596 A | \* | 9/1981 | Rubinstein ............... 128/270 |
| 4,935,004 A | | 6/1990 | Cruz |
| 4,950,258 A | | 8/1990 | Kawai et al. |
| 5,112,305 A | | 5/1992 | Barath et al. |
| 5,354,279 A | | 10/1994 | Hofling |
| 5,364,356 A | | 11/1994 | Hofling |
| 5,376,376 A | \* | 12/1994 | Li .......................... 424/443 |
| 5,419,760 A | \* | 5/1995 | Narciso, Jr. .................. 604/8 |
| 5,419,777 A | | 5/1995 | Hofling |
| 5,536,250 A | | 7/1996 | Klein et al. |
| 5,591,159 A | | 1/1997 | Taheri |
| 5,599,292 A | | 2/1997 | Yoon ........................ 604/11 |
| 5,599,306 A | | 2/1997 | Klein et al. |
| 5,649,902 A | \* | 7/1997 | Yoon ......................... 604/1 |
| 5,681,281 A | | 10/1997 | Vigil et al. |
| 5,693,029 A | | 12/1997 | Leonhardt |
| 5,709,874 A | | 1/1998 | Hanson et al. |
| 5,741,297 A | \* | 4/1998 | Simon ..................... 606/213 |
| 5,871,484 A | \* | 2/1999 | Spievack et al. .......... 606/60 |
| 5,873,865 A | | 2/1999 | Horzewski et al. |
| 5,895,407 A | \* | 4/1999 | Jayaraman .............. 606/198 |
| 6,030,375 A | \* | 2/2000 | Anderson et al. ....... 604/890.1 |
| 6,036,666 A | \* | 3/2000 | Peiler et al. ............... 604/11 |
| 6,053,900 A | | 4/2000 | Brown et al. |

\* cited by examiner

*Primary Examiner*—Sharon Kennedy (57) ABSTRACT

An apparatus and method for selectively delivering a medicament to a target location of the wall of a body cavity, blood vessel, or the like, comprising a compressed hollow cylinder of permeable, expandable foam, attached to the distal end of a delivery device such as a catheter or catheter guidewire. Using the delivery device, the compressed cylinder is advanced to a target location within the body, and the compressed foam cylinder is allowed to expand so as to contact the walls of the body cavity, blood vessel, or the like, while allowing bodily fluids to freely flow through the central lumen of the cylinder. The foam cylinder is provided with means for perfusing it with a medicament so that the medicament is placed in contact with the walls of the patient's anatomy, and is also provided with means for preventing the medicament from entering the patient's bloodstream.

59 Claims, 5 Drawing Sheets

MEDICAMENT DELIVERY SYSTEM

BACKGROUND OF THE INVENTION

1. Field of the Invention

This invention relates to methods for the introduction of medication to specific points in the body. More particularly, the present invention relates to an improved apparatus and method for selectively delivering medication to a specifically targeted wall section of a blood vessel, body cavity, or the like, so as to allow more accurate medication of specific ailments.

2. State of the Art

There are a wide variety of known methods for introducing medication into the body, such as injestion, hypodermic injection, transdermal application, inhalation, and intravenous injection. However, all of these methods result in systemic drug introduction. This is appropriate for many conditions, but not in others. In certain circumstances, it is desired to introduce a drug only at a specific site of an ailment within the body. In such cases, systemic drug introduction results in substantial overmedication in order to ensure that a sufficient dosage is available at the site of the ailment. This results in the unnecessary use of excess medication, and may also exacerbate side effects.

To address some of these problems, venous catheters and similar devices have been used to introduce medication at a specific site within a blood vessel, body cavity, or the like. The catheter is threaded through the anatomy to a point near to or at the site of a specific ailment, whereupon the medication is released from the catheter. This method, however, presents several drawbacks. In a flowing blood vessel, the medication is quickly drawn downstream from the intended application site. Thus, while medication will be available at the desired site, additional medication will flow systemwide, presenting the same drawbacks as in the case of systemic medication mentioned above. In other applications, a balloon catheter or other device may be used to stop blood flow in the vessel to prevent the medication from being swept systemwide. However, because blood flow can only be stopped for brief periods of time without causing damage to surrounding tissues, this method is not satisfactory for most applications.

Figure 1:
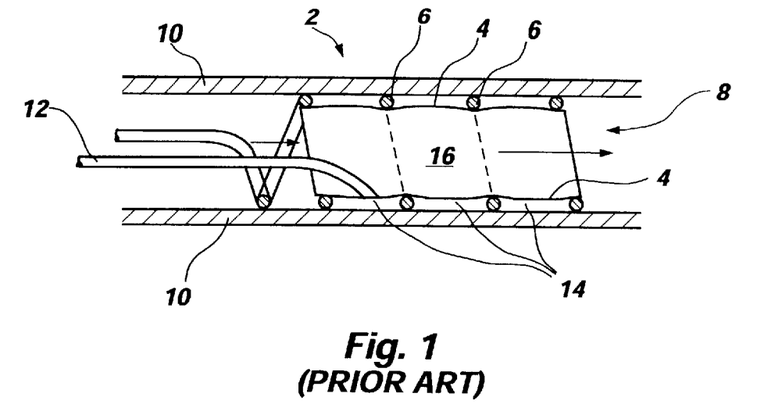
FIG. 1 shows a prior art medication delivery device comprising a helical tubular polymer coil with impermeable webbing stretched between adjacent coils.

To address these problems, devices have been developed which attempt to place medication at a targeted site and hold it there for an extended length of time without interfereing with blood flow. In some of these devices, a drug delivery apparatus is held in place within a vessel by means of barbs or other protrusions which extend out and grab the vessel wall. These devices are undesirable because of the trauma that they cause to body tissue. Another approach of prior art devices is shown in FIG. 1. This device utilizes a thin, inflatable coil tube, denoted generally at 2, having impermeable webbing 4 disposed between several of the coils 6 at or near the distal end 8 of the device. The distal portion 8 of the tube 2 is held against the sides of the blood vessel 10 by pressurizing the coil tube, and a medication supply tube 12 delivers medication to the space 14 between the webbing 4 and the vessel wall 10. This device may thus be held in contact with the vessel wall for an extended period of time, while blood flows essentially uninterrupted through the central lumen 16 of the coil. However, the device of FIG. 1 also presents several drawbacks. First, it does not isolate the space 14 from the blood flow lumen 16 very well—i.e., it leaks. Additionally, the central lumen 16 may not be large enough to accommodate the necessary blood flow. Finally, the device is complicated and expensive to manufacture.

There is thus a need for an a traumatic method of selectively introducing medication into a wall section of a body cavity, blood vessel or the like that allows the medication to remain in contact with the anatomy for an extended period of time as required, without causing trauma to body tissues, requiring the stoppage of blood flow, or resulting in needless systemwide introduction of medication.

OBJECTS AND SUMMARY OF THE INVENTION

It is therefore an object of the present invention to provide an a traumatic apparatus and method for selectively delivering medication to a target location of a body cavity, blood vessel, or the like that does not result in significant quantities of the medication being swept downstream and introduced into the body systemwide.

It is another object of this invention to provide an apparatus and method for selectively delivering medication to a target location of a body cavity, blood vessel, or the like that does not stop the flow of blood or fluid within the anatomy in order to give the medication time to be absorbed.

It is another object of this invention to provide an apparatus and method for selectively delivering medication to a target location of a body cavity, blood vessel, or the like that allows the medication to circulate through the device so as to provide a constant concentration of the medication at the vessel/device interface.

The above and other objects are realized in an apparatus comprising a compressed hollow cylinder of permeable, expandable foam, attached to the distal end of a delivery device such as a catheter or catheter guidewire. The delivery device is for introducing the compressed cylinder into the patient's anatomy, whereby the compressed foam cylinder may be advanced to a point adjacent to a target location where medication is needed. The compressed foam cylinder is provided with means for expanding it within the body cavity, blood vessel, or the like, so as to contact the walls of the body cavity, blood vessel, or the like with its outside surface so that a medicament may be placed in contact with the walls of the patient's anatomy, while allowing the patient's bodily fluids to freely flow through the central hollow or lumen of the cylinder. The cylinder is provided with means for perfusing it with a medicament, such as an infusion tube which extends along the delivery device, and terminates at its distal end within the foam material, whereby medicament may be introduced into the proximal end of the infusion tube and may be released from the distal end to perfuse into the foam material. The apparatus may also be provided with a second lumen for withdrawing or circulating the medicament from or through the foam. This greatly reduces spillage if the fluid is removed from the medicament delivery volume at the same rate as it is infused into it. The apparatus is also provided with means for preventing the medicament from entering the patient's bloodstream.

In one embodiment, the foam cylinder is compressed by means of a sheath disposed thereabout, and the means for expanding the cylinder within the patient's anatomy comprises one of various means for opening and pulling the sheath off of the foam cylinder. In an alternative embodiment, the sheath is soluble in water or other fluid so that it breaks down within the patient, thereby allowing the hydrophillic foam cylinder to expand. In still another embodiment, the medicament is preloaded into the foam material and released when the protective sheath is removed from the foam cylinder.

These and other objects are also realized in a method for selectively delivering medication to a target location of a body cavity, blood vessel, or the like comprising the steps of obtaining an apparatus for delivering said medicament as described, introducing the apparatus into the anatomy of the patient, directing the apparatus to an anatomical location in need of medicament, expanding the cylinder within the patient so as to contact the walls of the body cavity, blood vessel, or the like with the outside of said foam cylinder, while allowing the patient's bodily fluids to freely flow through the central hollow of said cylinder, delivering a medicament to the target location by perfusing the medicament into the foam material, and allowing the medicament impregnated foam to remain in contact with the walls of the patient's body cavity, blood vessel, or the like for sufficient time to be absorbed thereby, and then removing the apparatus from the patient's anatomy following use.

These and other objects are also realized in a method for manufacturing said apparatus.

Other objects and features of the present invention will be apparent to those skilled in the art, based on the following description, taken in combination with the accompanying drawings.

DETAILED DESCRIPTION OF THE PREFERRED EMBODIMENT

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 2A:
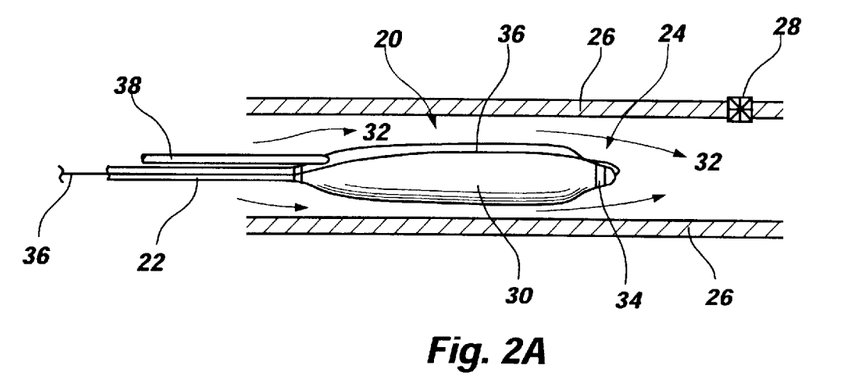
FIG. 2A shows a medication delivery device according to the present invention which is disposed upon the end of a guide wire and being directed to a target location.
Figure 2B:
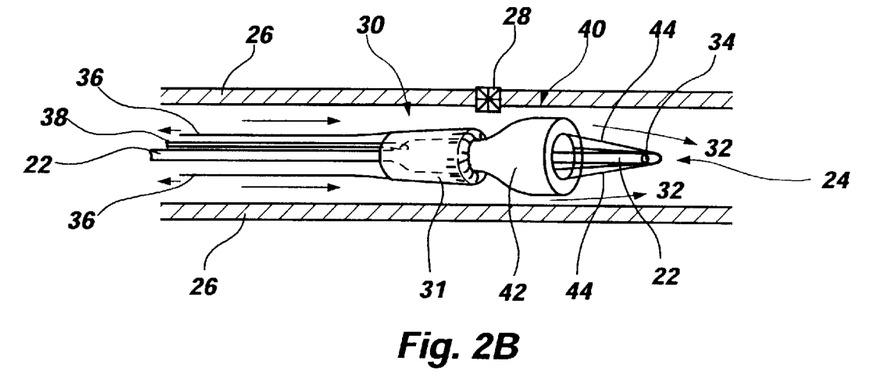
FIG. 2B shows the medication delivery device of FIG. 2A at the target location in the process of the sheath surrounding the foam cylinder being opened by inverting and pulling back with the attached filaments, while the cylinder expands to meet the vessel walls.
Figure 2C:
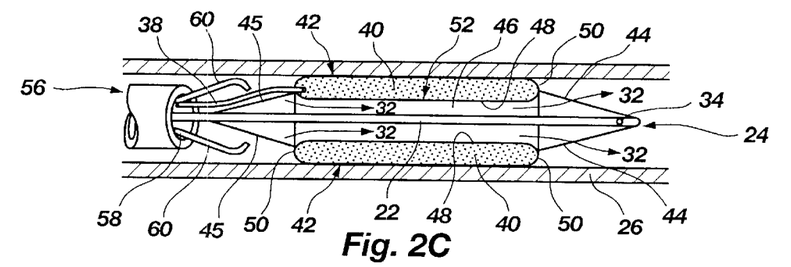
FIG. 2C shows a cross section of the present invention in place at the target location, with the foam cylinder fully expanded and contacting the vessel walls.

FIGS. 2A through 2C depict one embodiment of the apparatus and general sequence of steps in the method of the present invention. FIG. 2A shows the medication delivery device, denoted generally at 20, disposed upon the distal end 24 of a delivery device 22 such as a catheter or catheter guide wire. The apparatus is being directed through a bodily opening, such as a blood vessel 26, to a target location 28 where medication is needed. It will be apparent that this invention is not limited to use in blood vessels, but can be introduced into a variety of bodily openings or cavities, such as an ear canal, nasal passages or sinuses, portions of the gastrointestinal system, the abdominal or chest cavity, the urinary tract, reproductive organs, etc.

As depicted in FIG. 2A, the apparatus is initially tightly compressed about the end of the guidewire 22 by a sealed sheath 30, such that its size is smaller than the diameter of the vessel, and no fluid may contact the device until after the seal is broken. This configuration allows blood or other fluid flow, denoted by arrows 32, to freely continue around the device during insertion. The distal tip of the guidewire 22 or other delivery device may advantageously be provided with a radiopaque band 34 to aid the physician in directing the device to the desired target location during insertion. The medication delivery device 20 also includes at least one filament 36 attached to the distal end of the sheath 30, and a medication infusion tube 38.

In one embodiment, as shown in FIG. 2B, once the device 20 is guided to the target location 28, the filaments 36 are pulled from the proximal end to break the seal of the sheath 30 at its distal end. Continued pulling on the filaments 36 causes the sheath 30 to open from the distal end and invert as it is pulled toward the proximal end thereof, to release a compressed foam cylinder 40. The inside surface of the sheath 31, or the outside surface of the cylinder 42, or both, are preferably treated with a biocompatible lubricious coating, such as a hydrophillic material, to provide lubrication as needed to ease the process of pulling back the sheath. Once pulled from around the foam cylinder 40, the sheath 30 is preferably pulled to the proximal end of the delivery device 22 by means of the filaments 36, and entirely removed from the patient's body. It will be apparent that other means of removing the sheath may be provided, as described in detail below.

As shown in FIG. 2B, once the sheath 30 is removed, the cylinder 40 expands to meet the vessel walls 26. Once expanded, the structure of the apparatus 20 becomes more apparent. Contained within the sheath 30 is a hollow foam cylinder 40, formed of a soft, spongy, open cell material which can hold medication. The cylinder 40 may be formed to accommodate medicines in various forms, such as liquids, powders, or pellets. It is preferably formed of a urethane foam material which may be tightly compressed, but will expand to its original shape and size when the compressive force of the sheath is released. Alternatively, the cylinder 40 may be formed of a hydrophillic foam material that expands to much more than its original size when in an aqueous solution, such as blood. Alternatively, the cylinder 40 may be constructed of cellulose or other foam that can be dried in a compressed condition, and will remain in that shape until it is wetted again. As still another alternative, the cylinder 40 may be formed of a urethane or other foam material, which is then provided with a coating to change the surface properties of the foam. For example, a coating which makes the ordinary urethane hydrophillic so as to expand in an aqueous solution may be added. Alternatively, coatings which change the structural properties of the foam may also be provided, such as a coating which makes the foam cylinder stiffer.

From FIGS. 2B and 2C some other structure of the present device also becomes visible. The distal end of the delivery device 22 is provided with tethers 44 which connect the tip of the delivery device to the distal end of the foam cylinder 40. The proximal end of the cylinder is also connected to the delivery device 22 by tethers 45 as shown in FIG. 2C. These thethers advantageously allow the expanded foam cylinder 40 to remain attached to the delivery device 22, while allowing it to expand away from it. This provides a central lumen 46 for uninterrupted blood or other fluid flow, denoted by arrows 32, while still providing a strong connection to the delivery device. This configuration advantageously allows the physician or other user to manipulate the drug delivery device if needed after it has expanded in the vasculature, and also facilitates removal of the device as described below. It will be apparent that, as oppositely oriented thin tension members, the tethers 44 and 45 must be strong enough to connect the foam cylinder 40 to the guidewire 22 in a pressurized, flowing environment, and also in anticipation of friction with the side walls of the vessel.

Once the sheath is entirely removed, the cylinder 40 expands to press against the vessel walls, and deliver its medication, while allowing blood to flow through the central lumen 46. FIG. 2C provides a cross section of the cylinder 40 and related structure when in place at the target location, with the foam cylinder fully expanded and contacting the vessel walls. In this view the tethers 44 and 45 are clearly visible in their extended orientation. The foam cylinder 40 is preferably in the shape of a hollow cylinder, having an outside medication delivery surface 42 for contact with the wall of a body cavity, blood vessel or the like, an inside surface 48 proximal to the guidewire 22, and annular end surfaces 50. As shown in FIG. 2C, the inside surface 48 and annular end surfaces 50 are preferably coated with a non-porous skin 52, which prevents outflow of the medication except toward the vessel walls. This configuration provides one of the great advantages of the present invention by keeping the medication in contact with the delivery site in an atraumatic manner, but preventing it from entering the blood and flowing downstream. A small portion of the outside surface 42 immediately adjacent to the annular end surfaces 50 may also be provided with this skin 52 so as to ensure a positive seal between the foam cylinder and the vessel wall. There are a number of methods of forming the skin 52, which will be described in more detail below.

As depicted in FIG. 2C, medication is preferably provided to the foam cylinder by means of an infusion tube 38, which follows the delivery device 22 and delivers the medication directly into the foam cylinder 40. It will be apparent that more than one infusion tube 38 may be provided, or the infusion tube may have multiple openings or delivery points into the foam material to provide more uniform saturation of the foam material with the medication. Additionally, a pair of infusion tubes may be advantageously provided to allow medication to be introduced through one tube and extracted through the other, thus allowing medication to be circulated through the foam material for more complete and uniform exposure of the body cavity wall to the medication. Alternatively, the foam material or the skin of the foam material may be pre-loaded with a medication, which is naturally absorbed by the wall of the blood vessel or the like when the foam cylinder is placed in contact with it. Such medications may be provided in the form of powders, pellets, or liquid as described above. It will be apparent that pre-loading of the medication avoids the need for an infusion tube, which helps reduce the overall size of the apparatus, making introduction into the patient's anatomy easier and less intrusive. A pre-loaded medication is advantageously protected from contact with and dispersal into the bloodstream during introduction of the device by the sealed sheath 30.

Because of its soft, atraumatic design and construction, once the medication delivery process is complete, the entire apparatus 20 can be removed simply by pulling on the proximal end of the guidewire 22 to remove it from the patient. Because the tethers 44 and 45 are strong enough to withstand the forces created by friction with the sidewalls of the vessel 26, the apparatus cannot become detached from the delivery device and lodge within the patient. Alternatively, a hollow catheter 56 with an openable mouth 58 may be threaded over the guidewire 22, and the guidewire 22 and drug delivery apparatus 20 may be pulled inside the catheter and removed from the patient. This method provides the advantage that the catheter 56 may remain in place for subsequent procedures if desired. Alternatively or additionally, the catheter 56 may be provided with a grabbing device, such as spring loaded protrusions 60 or a bag (not shown), to capture the foam device 20 and pull it into the mouth of the catheter 56. It will be apparent that the medication delivery apparatus 20 may also be initially introduced into the patient by means of such a catheter 56, rather than a guidewire 22. In such an alternative configuration, the catheter 56 could contain a guidewire within, and the apparatus 20 could be removed from the patient by removing the catheter along the guidewire, leaving the guidewire in place to facilitate subsequent procedures.

Figure 3:
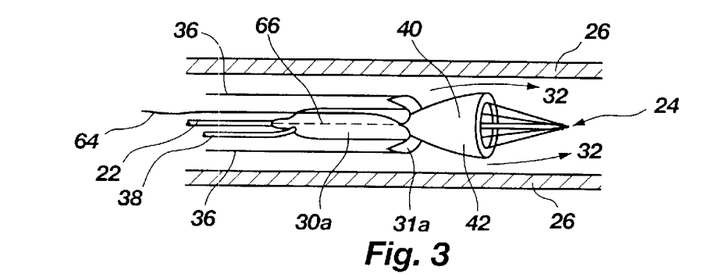
FIG. 3 shows a medication delivery device according to the present invention wherein the foam cylinder is compressed by a sheath which is opened by means of a "rip cord" filament.

As noted above, there are various means of opening and removing the sheath 30. FIG. 3 shows a medication delivery device according to the present invention wherein the foam cylinder is compressed by a sheath 30a which is opened by means of a "rip cord" filament 64. This sheath 30a is provided with a longitudinally oriented weakened area 66. The "rip-cord" filament 64 is attached to either the proximal end of the foam cylinder 40, or to the guidewire 22 near the proximal end of the cylinder, and is disposed between the outer surface of the foam cylinder 42 and the inner surface 31a of the sheath 30a in the weakened region. The "rip cord" filament 64 then passes through the end seal of the sheath at the distal end, and doubles back along the delivery device to its proximal end, where a user may grasp and pull it. Initial pulling on the "rip cord" causes the end seal to break, and continued pulling cuts the sheath along the weakened region. Additional filaments 36 are advantageously provided to allow the sheath to be inverted and pulled from around the cylinder and out of the patient in a manner similar to that described above.

The longitudinally oriented weakened region 66 of the sheath 30a may be formed in many different ways. The weakened region 66 may comprise a line of full depth perforations, partial depth perforations, a thinned section, or any other method which will allow the "rip cord" filament 64 to cut the sheath 30a.

Figure 4:
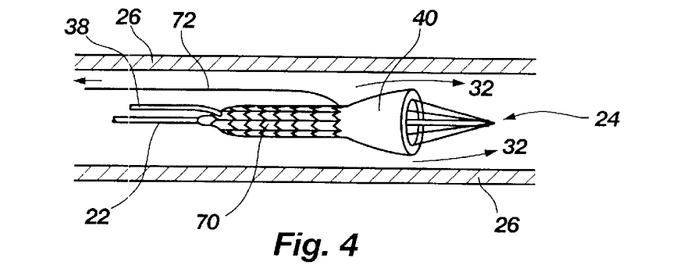
FIG. 4 shows a medication delivery device according to the present invention wherein the foam cylinder is compressed by a knit sheath which is opened by pulling one cord to unravel it.

FIG. 4 shows an alternative sheath configuration of the present invention wherein the foam cylinder 40 is compressed by a knit sheath 70. This sheath is formed of a single cord 72 which is knit or sewn into a tubular configuration having sufficient strength to hold the cylinder 40 in its compressed configuration. At the distal end of the sheath, the end of the single cord 72 doubles back along the delivery device 22 to its proximal end, where a user may grasp and pull it. When the user does so, the knit sheath 70 begins to unravel, progressively allowing the cylinder 40 to expand to fill the body cavity, and allowing the cord 72 to be completely removed from the patient.

Figure 5:
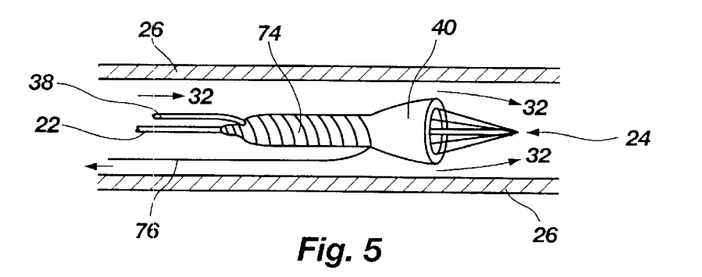
FIG. 5 shows a medication delivery device according to the present invention wherein the foam cylinder is compressed by a helically wound sheath which is opened by pulling one cord to unwind the sheath.

FIG. 5 shows another alternative embodiment of the medication delivery device of the present invention wherein the foam cylinder 40 is compressed by a helically wound sheath 74. Like the knit sheath of FIG. 4, the helically wound sheath 74 is preferably formed of a single cord 76, which doubles back from its distal end along the delivery device 22 to the proximal end thereof, where a user may grasp and pull it. When the user does so, the helically wound sheath 74 begins to unwind, progressively allowing the cylinder 40 to expand to fill the body cavity, and allowing the helical cord 76 to be completely removed from the patient. It will be apparent that in the embodiments of both FIG. 4 and FIG. 5, the compressed cylinder is not sealed from contact with bodily fluids prior to release of the sheath, unlike the other embodiments of the present invention.

Figure 6:
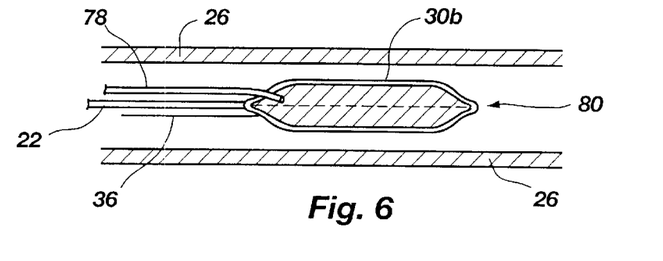
FIG. 6 shows a medication delivery device according to the present invention wherein the foam cylinder is compressed by a sheath under vacuum pressure, and which is opened by breaking the vacuum seal and pushing the foam cylinder beyond the sheath.

FIG. 6 shows another embodiment of the present invention wherein the foam cylinder 40 is held in a sheath 30b which is compressed by means of vacuum pressure. The vacuum pressure may be applied by any suitable method, such as by a vacuum tube 78 connecting the space inside the sheath to a vacuum pump or syringe (not shown) outside of the patient. To open the sheath and expose the delivery device 20, the internal vacuum is released, allowing the closed distal end 80 of the sheath 30b to open. The foam cylinder 40 may then be pushed through the open end 80 of the sheath, to allow it to expand in the body cavity. Filaments 36 are preferably embedded in the proximal end of the sheath 30b to allow it to be pulled backward and out of the patient while the foam cylinder 40 is pushed forward by the guidewire 22 or other delivery device. It will be apparent that after release of the vacuum and expansion of the foam cylinder 40, the vacuum tube 78 may advantageously be used as an infusion tube to provide the medication to the foam cylinder.

Figure 7A:
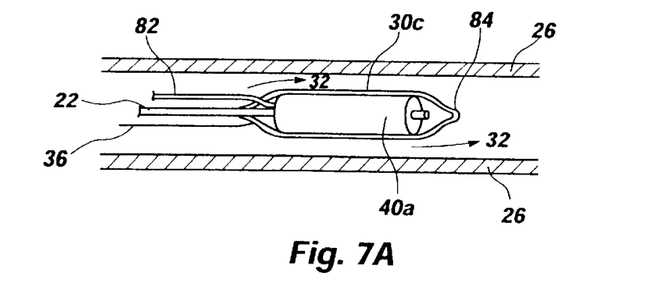
FIG. 7A shows a medication delivery device according to the present invention wherein the foam cylinder is formed of a compressed swelling foam, and the sheath is opened by means of pushing the guidewire and foam forward to puncture the end of the sheath.

FIG. 7A shows a medication delivery device according to the present invention wherein the foam cylinder 40a is formed of a compressed swelling foam. and the foam cylinder 40a is formed of a swelling foam material. It will be apparent to one skilled in the art that the foam could be a non-swelling foam which is impregnated with a hydrophillic material that absorbs water from the blood or other bodily fluid, and expands to the required therapeutic size. In the embodiment of FIG. 7A, the foam cylinder 40a is protected from liquid, until release is desired, by a protective sealed sheath 30c. A lumen in the guidewire 22 or a separate tube 82 operates as an infusion tube to supply medicament to the foam tube 40a.

The sheath 30c is opened by means of pushing the guidewire 22 and foam 40a forward to puncture the distal end 84 of the sheath. The sheath 30c is prevented from forward motion by one or more filaments 36 that run through the catheter and out its proximal end, and which allow the sheath 30c to be retracted and removed from the patient so that the cylinder 40 may expand. The distal tip of the guidewire 22 may be advantageously formed in a pointed configuration so as to more easily puncture the seal at the distal end of the sheath.

Figure 7B:
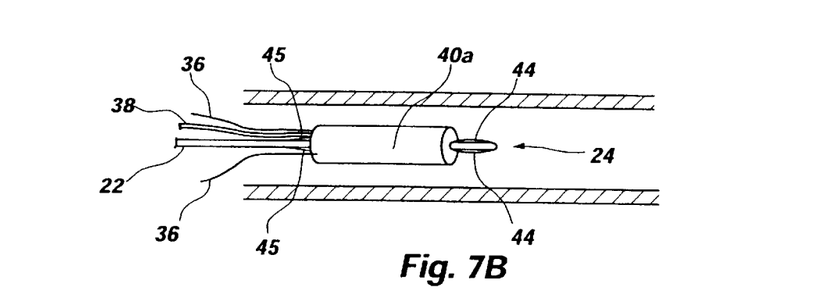
FIG. 7B shows a medication delivery device similar to that depicted in FIG. 7A, wherein the compressed swelling foam cylinder is not surrounded by a protective sheath.

FIG. 7B shows a medication delivery device similar to that depicted in FIG. 7A, wherein the compressed, swelling foam cylinder 40a is not surrounded by a protective sheath, but is simply introduced into the patient in its exposed condition. In this embodiment, the cylinder 40a is designed to swell at a rate such that it may be introduced into the patient and directed to the target location before it swells to its therapeutic size and causes excessive friction with the patient's internal anatomy. As with the above described embodiments, the cylinder 40a is provided with an infusion tube 38, or alternatively, may be preloaded with a medication. The cylinder is shown attached to the delivery device via tethers 44 and 45, such that it may be removed following the medication delivery procedure. However, retraction filaments 36 may be alternatively provided, which allow the cylinder to be removed independently of the delivery device.

The embodiment of FIG. 7B also highlights another alternative configuration of the present invention. With the foam cylinder 40a attached to the end of the delivery device 22 without a compressive outer sheath, it will be apparent that some method of attachment between the delivery device and the cylinder is needed to ensure that the cylinder is firmly attached as it is being advanced into the patient. While the distal tethers 44 could conceivably perform this function, this would be less than satisfactory. To solve this problem, the foam cylinder 40a may be attached to the distal end of the delivery device 22 by means of a soluble bonding agent disposed between the inside surface 48 of the foam cylinder and the outside surface of the distal end of the delivery device. This bonding agent is configured to dissolve in the patient's internal environment, allowing the foam cylinder to expand away from the delivery device to contact the walls of the body cavity, blood vessel, etc. It will be apparent that the boding agent between the inside surface 48 of the foam cylinder and the outside surface of the delivery device must be configured to dissolve at a rate that is somewhat faster than the rate of expansion of the expanding foam cylinder to prevent the foam cylinder from expanding to contact the walls of the body cavity while still connected to the delivery device, resulting in total blockage of the body cavity or blood vessel. It will also be apparent to one of skill in the art that the use of a soluble bonding agent between the foam cylinder and the delivery device could advantageously be employed in many of the other embodiments of the present invention described herein.

Figure 8:
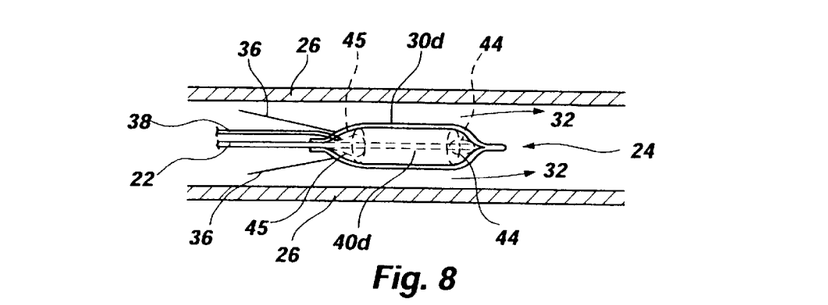
FIG. 8 shows a medication delivery device according to the present invention wherein the sheath is formed of a material which dissolves when exposed to bodily fluids such as blood.

FIG. 8 shows another embodiment of the present invention wherein the sheath 30*d* is formed of a soluble biocompatible material which will dissolve when exposed to bodily fluids such as blood, water, etc. In this embodiment, the sheath material may be formulated and formed so as to dissolve at a desired rate, allowing the user adequate time to position the device 20 within the patient. In this embodiment the foam cylinder 40*d* may comprise the conventional compressed urethane or other foam material discussed above, or may be the swelling foam, which is protected from liquid until the sheath dissolves. It will also be apparent that the drug delivery device may be pre-loaded with medication as discussed above, or may comprise an infusion tube 38 to deliver medication to the cylinder.

Figure 9A:
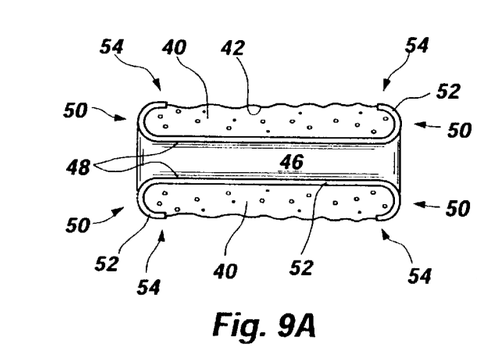
FIG. 9A shows a cross-sectional view of a foam cylinder having a molded-on skin to isolate the drug delivery area from contact with the patient's blood flow.

FIG. 9A shows a cross-sectional view of a foam cylinder 40 showing the skin 52 which isolates the drug delivery area from contact with the patient's blood flow. This view clearly shows the outside surface 42 of the sheath, which is intended to contact with the wall of the body cavity, blood vessel or the like, so as to deliver the medication. The inside surface 48 and annular end surfaces 50 are coated with a nonporous skin 52, which prevents outflow of the medication, except toward the cavity walls. The skin 52 may be formed of latex or cellulose, but urethane is preferred. In the preferred embodiment, a small area 54 of the outside surface 42 immediately adjacent to the annular end surfaces 50 is also coated with the skin so as to provide a better seal between the cylinder 40 and the cavity wall.

Figure 9B:
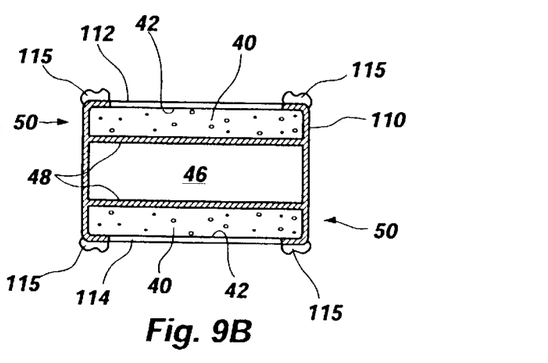
FIG. 9B shows a cross-sectional view of a foam cylinder having a skin that is formed by coating the inside and end surfaces of the cylinder with a gel material which seals the surface of the foam material.

In the embodiment of FIG. 9A, the skin 52 is molded onto the foam cylinder 40. This may be done in several ways. For example, the foam cylinder may be formed by an extrusion or molding process which forms a skin on the inside diameter of the cylinder. Then, a skin may be bonded to the annular end surfaces, or the annular end surfaces may be coated with a gel that swells into the surface cavities of the foam and seals it. Alternatively, the foam cylinder may be formed by injection of foam material into a mold already having a skin formed therein. Yet another alternative is to form the foam cylinder without a skin, and then bond a separately made skin onto it. This may be done by dip coating a formed skin with foam material. Alternatively, it may be done by dip coating a formed foam cylinder into skin material. As yet another alternative, the skin may be formed on the surface of a separately formed foam tube by inverting a formed foam cylinder to expose the inside diameter, spray coating a skin material thereon, then re-inverting it. Finally, the skin may be applied by compressing the cylinder, freezing it, then die cutting it to form the skin FIG. 9B shows a cross-sectional view of a foam cylinder 40 having a skin 110 that is formed by coating the inside and end surfaces 48 and 50 of the cylinder with a gel material which seals the surface of the foam material. This coating may be applied by any of the methods described above. This gel material penetrates the open cell structure of the surface of the foam, and forms a water tight barrier which prevents the medication from escaping from the foam into the bloodstream. Urethane hydrogel is presently preferred as this gel material to form the coating, but any material that is very flexible and swells in contact with water and bonds to the foam will perform properly according to the objects of this invention.

In any of the embodiments of this invention, the outer surface 42 of the foam cylinder may be coated with a porous outer skin 112, as shown in FIG. 9B. This coating may be formed of hydrophillic urethane or silicone rubber, and acts to reduce thrombus formation around the foam. Alternatively, the porous outer skin 112 may be provided with a plurality of check valves 114 which allow medicament to flow out, but prevent fluids from flowing into the foam material. These check valves could be formed as small flaps in a hydrophillic urethane membrane that forms the outer skin 112.

Figure 10A:
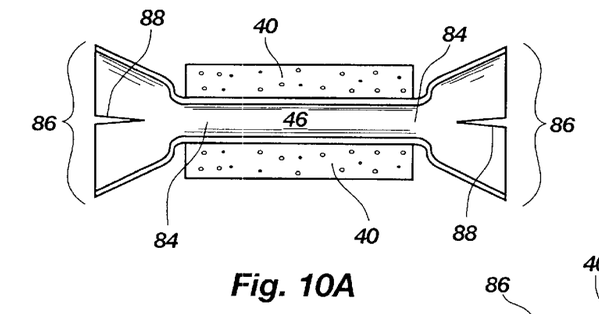
FIG. 10A shows a cross-sectional view of a foam cylinder which is bonded to a separately formed skin with non-inverted end seals.
Figure 10B:
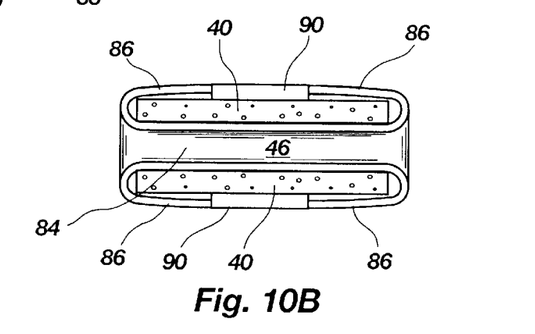
FIG. 10B shows a cross-sectional view of a foam cylinder which is bonded to a separately formed skin with inverted end seals.

There are several ways that a foam cylinder may be bonded to a separately formed skin, one of which is depicted in FIGS. 10A and 10B. FIG. 10A shows a cross-sectional view of a foam cylinder 40 which is bonded to a separately formed skin 84 with non-inverted end seals 86. The skin 84 is formed first, then the foam material is placed thereon to form a cylinder. The non-inverted end seals 86 have slits 88 to facilitate inversion over the ends of the foam cylinder 40, and to accommodate a range of vessel diameters. Once the foam material is in place, the end seals may be inverted to wrap around the ends of the cylinder, as shown in FIG. 10B. Tethers 90 may be provided to attach opposing edges of inverted end seals to prevent them from univerting. Alternatively, the end seals may be bonded to the foam cylinder 40 in the inverted position by means of a biocompatible bonding agent.

Figure 11:
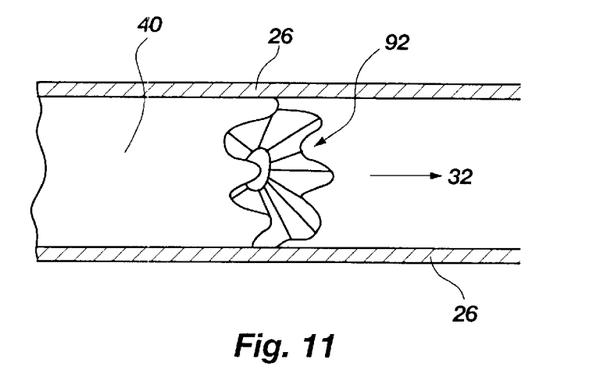
FIG. 11 shows an end view of a foam cylinder according to the present invention having a convoluted end to promote better adaption of the foam to varying vessel diameters.
Figure 12:
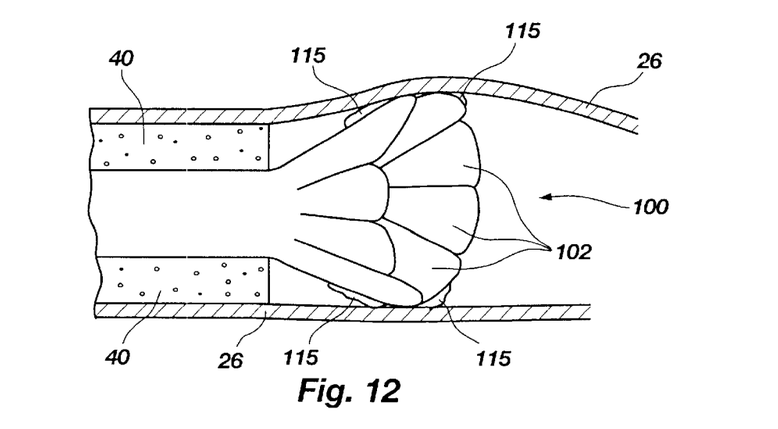
FIG. 12 shows a medication delivery device according to the present invention having an end seal formed of a plurality of radially oriented petals to promote better adaption of the foam to varying vessel diameters.

FIG. 11 shows an end view of a foam cylinder 40 according to the present invention having a convoluted or corrugated end 92. This configuration promotes better adaptation of the foam cylinder 40 to varying diameters and irregularities of the vessel 26 because the skinned surface expands and contracts in a more coordinated fashion than it would without the convolutions. In one embodiment the convolutions 92 may be biased against the vessel walls by means of a spring disposed within the distal end of the foam cylinder. Alternatively, FIG. 12 shows the medication delivery device of the present invention having a non-inverted end seal 100 formed of a plurality of radially oriented petal-shaped lips 102. This configuration also promotes adaptation of the foam cylinder 40 to varying diameters and irregularities of the vessel 26. The petals 102 may expand non-uniformly to contact the walls of the vessel, sealing the edges of the cylinder to prevent migration of the medication into the bloodstream. This embodiment may also be spring loaded, or may rely solely on the resiliency of the material from which the petal-shaped lips are formed for biasing against the vessel walls. In any of the embodiments of this invention, including those of FIG. 11 or FIG. 12, the end surfaces of the foam cylinder or the lips may be coated with a hydrophillic gel which occludes the foam material and promotes a better seal between the apparatus and the vessel walls while preventing leakage of the medicament from the foam material. FIG. 9B and FIG. 12 show the typical placement of this hydrophillic gel 115 on the end surfaces of the foam cylinder 40 or petal shaped lips 102 so as to enhance the seal between the device and the vessel wall 26.

In lieu of or in addition to the expansive force of the foam cylinder, the medication delivery device of this invention may be provided with inner support means for providing a force for biasing the foam cylinder against the walls of the body cavity. This may be done in several ways. In the embodiment of FIG. 9A and FIG. 9B, the skin 48 forming the central lumen 46 of the device and the end surfaces 52 may be formed of a resilient material which, after the release of the compressive force of the outer sheath or similar means for compressing the foam cylinder 40, will expand to resume its uncompressed shape. This expansion will help provide cylindrical support to the device.

Figure 13A:
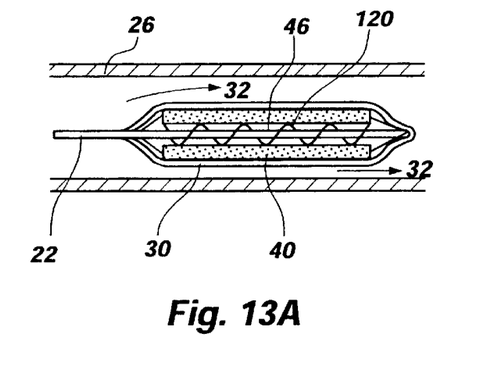
FIG. 13A shows a medication delivery device according to the present invention in its compressed state having a helical coil within the central lumen of the compressed foam cylinder.
Figure 13B:
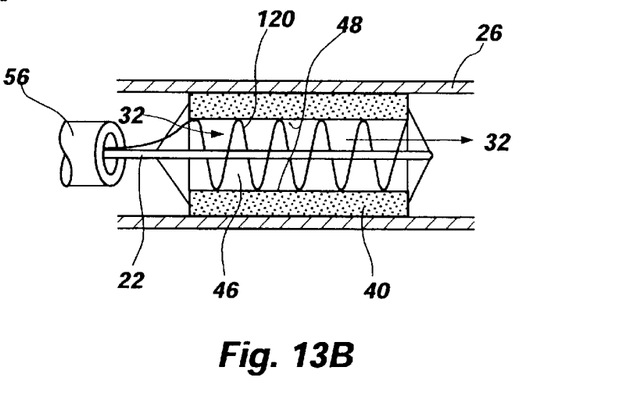
FIG. 13B shows a medication delivery device according to the present invention in its expanded state wherein the helical coil has expanded to provide inner support to the foam cylinder.

Alternatively, other means of providing inner support to the cylinder may be provided. One such alternative is shown in FIGS. 13A and 13B, wherein a helical coil 120 of thin superelastic ribbon is disposed within the central lumen 46 of the foam cylinder 40. In FIG. 13A, when the foam cylinder 40 is compressed by a sheath 30, the helical coil 120 is also compressed within the lumen 46. Once the compressive force of the sheath or other means is released, the foam cylinder 40 expands, as shown in FIG. 13B, assisted in part by the coil 120 which also expands, pushing on the interior surface of the central lumen 46. The helical coil 120 may be advantageously configured to be pulled into the lumen of a catheter 56, or alternatively, a lumen formed in the delivery device 22 itself. This will allow a user of the device to remove the inner support means following proper placement and expansion of the foam cylinder at the intended site of medication delivery.

Figure 14:
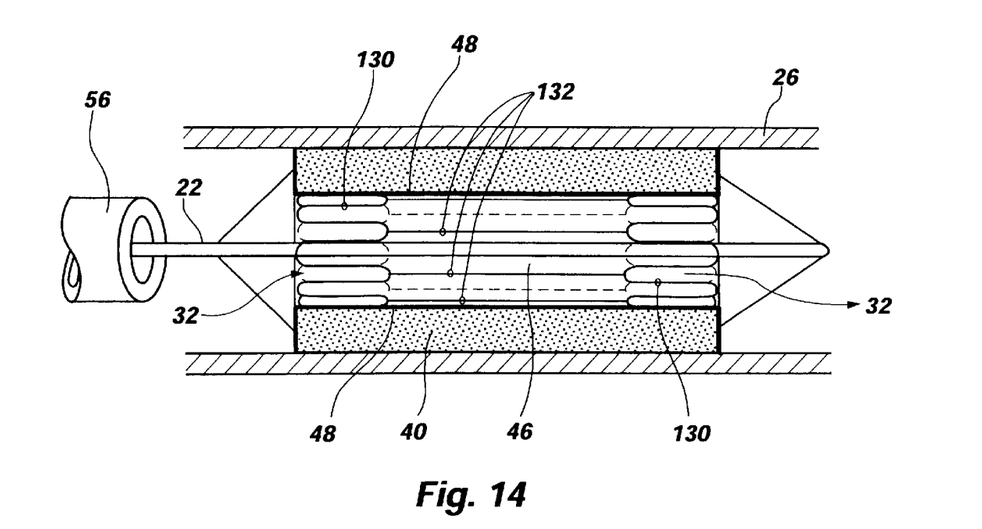
FIG. 14 shows a medication delivery device according to the present invention in its expanded state having a pair of serpentine coils connected by connecting rails to provide inner support to the foam cylinder.

FIG. 14 depicts another alternative means of providing an inner support for the foam cylinder. In this embodiment, the cylinder 40 is provided with a pair of serpentine coils 130 which expand radially and press against the inside surface 48 of the lumen 46. The coils 130 are connected by a plurality of longitudinal connecting rails 132 which connect adjacent nodes of the opposing coils 130. The rails 132 are preferably oriented parallel to the delivery device as shown, and are drawn away from the delivery device 22 as the serpentine coils expand. Like the embodiment of FIG. 13, when the foam cylinder 40 is compressed by a sheath or other means, the serpentine coils 130 are also compressed within the lumen 46, and held tightly around the delivery device 22. Once the compressive force is released, however, the foam cylinder 40 expands, assisted by the serpentine coils 130 and connecting rails 132, which also expand, pushing on the interior surface of the central lumen 46. It will be apparent that instead of a pair of serpentine coils connected by connecting rails, a plurality of unconnected serpentine coils could be provided along the length of the central lumen, or alternatively, a single serpentine coil which extends the length of the lumen could be provided to accomplish the same ends. Also as in the embodiment of FIG. 13, the serpentine coils 130 and connecting rails 132 may be advantageously configured to be pulled into the lumen of a catheter 56, allowing a user of the device to remove the inner support means following proper placement and expansion of the foam cylinder at the intended site of medication delivery.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A medicament delivery system configured for selectively delivering a medicament to a target location in a body lumen of a patient comprising:

a resilient hollow cylinder of permeable foam, said cylinder having an outer surface, a central lumen, and proximal and distal ends, the cylinder defining proximal and distal openings of the central lumen and a fluid pathway therethrough, enabling fluid flow through the body lumen past the cylinder via the central lumen;

a delivery device configured for introducing the cylinder into the patient's body lumen, said delivery device having a proximal end and a distal end, and said cylinder being compressed and attached near the distal end of said delivery device to enable advancement of the cylinder into the patient's anatomy for placement adjacent the target location;

a sheath disposed over the cylinder and configured to be pulled open from a distal end thereby allowing for expanding the cylinder within the body cavity, the apparatus being configured to selectively allow said compressed cylinder to expand to contact the walls of the body lumen when said cylinder has been placed adjacent to the target location; and a medicament absorbed by the hollow cylinder, whereby the medicament is placed in contact with a walls of the body lumen at said target location.

2. An apparatus as described in claim 1, wherein the foam cylinder comprises a material selected from the group consisting of urethane and a hydrophilic material.

3. An apparatus as described in claim 2, further comprising a coating applied to the outer surface of said cylinder, said coating comprising a material selected from the group consisting of: a hydrophillic material, an anti-thrombogenic material, a permeable anti-thrombogenic membrane material, a material which mechanically stiffens the cylinder, and a coating material which forms an impermeable seal on the surface of said foam material.

4. Apparatus as described in claim 1, further comprising a porous skin formed on the outer surface of said foam cylinder.

5. Apparatus as described in claim 4, further comprising check valves formed in said porous skin to allow medicament to flow out, but prevent fluids from flowing into the foam material.

6. Apparatus as described in claim 5, wherein said porous skin is formed of a hydrophillic urethane material, and said check valves comprise a plurality of flaps formed in said skin.

7. An apparatus as described in claim 1, wherein the delivery device is selected from the group consisting of a catheter and a catheter guidewire.

8. Apparatus as described in claim 7 wherein the means of attachment of said foam cylinder to the distal end of said delivery device comprises at least one tether connected between the distal end of the foam cylinder and the distal end of the delivery device, and at least one tether connected between the proximal end of the foam cylinder and the delivery device, whereby the compressed foam cylinder may be advanced through the patient's anatomy as the delivery device is so advanced.

9. Apparatus as described in claim 7 wherein said foam cylinder is attached to the distal end of said delivery device by means of a bonding agent which is soluble in bodily fluids.

10. Apparatus as described in claim 7 wherein the delivery device is a catheter having an opening at its distal end, said distal opening terminating within the foam material, whereby the means for perfusing said cylinder with a medicament comprises introducing a medicament into said catheter and allowing said medicament to flow into said foam material.

11. An apparatus as described in claim 1, further comprising at least one tube extending proximally from the cylinder along the length of the delivery device, said at least one tube having a first end which is configured to extend outside the patient and is configured to receive the medicament, and a second end disposed adjacent the foam cylinder, whereby medicament may be selectively introduced into said first end and through said tube to perfuse said foam cylinder, so as to cause the medicament to be brought into contact with the walls of said body lumen.

12. An apparatus as described in claim 11, comprising two hollow tubes which are configured in each case to extend proximally from the the first end along the length of the delivery device to the second end adjacent the foam cylinder, such that the medicament may be introduced into the first end of the first tube to perfuse said foam cylinder, and may be subsequently drawn from said foam cylinder into the second end of the second tube such that the medicament is circulated through said foam material.

13. Apparatus as described in claim 11 wherein said at least one tube comprises a plurality of perfusion ports in the second end thereof so as to provide multiple medicament entry points into said foam material.

14. An apparatus as described in claim 1, wherein the medicament comprises a drug pre-loaded into the foam material.

15. An apparatus as described in claim 1, wherein the sheath is dissolvable in bodily fluids.

16. An apparatus as described in claim 1 further comprising a tether attached to the distal end of the sheath, wherein the sheath is configured so that it is opened by inverting and pulling said sheath toward the proximal end of said delivery device, so as to remove it from around said compressed cylinder.

17. An apparatus as described in claim 1, wherein the sheath is formed of knit filaments, and at least one filament extends from the distal end of said knit sheath along the delivery device to the proximal end thereof, whereby an operator can pull said filament, causing the knit sheath to unravel and thereby allow the compressed cylinder to expand.

18. An apparatus as described in claim 1, wherein the sheath is formed of at least one helically wrapped filament, and at least one filament extends from the distal end of said sheath along the delivery device to the proximal end thereof, whereby an operator can pull said filament, causing the helical sheath to unwrap and thereby allow the compressed cylinder to expand.

19. An apparatus as described in claim 1, wherein the sheath is formed of braided filaments in tension, and at least one filament extends from the distal end of said sheath along the delivery device to the proximal end thereof, whereby an operator can pull said filament, causing the tension in said braided sheath to be released and thereby allow the compressed cylinder to expand.

20. An apparatus as described in claim 1, wherein said sheath has a sealed distal end and an interior thereof is under vacuum so as to tightly squeeze the foam cylinder within the sheath and maintain the sealed distal end; the apparatus further comprising a means for releasing the vacuum and means to open the sealed distal end and means to thereafter pull back open said sheath to allow the compressed cylinder to emerge from said sheath and expand within the patient's anatomy.

21. Apparatus as described in claim 20, wherein the means for opening the sealed distal end of the sheath comprises means for puncturing the sealed distal end of said sheath so as to cause it to open, said means for puncturing being contained within said sheath.

22. Apparatus as described in claim 1 wherein the foam cylinder has time dependent swelling characteristics, and the means for expanding the cylinder comprises introducing the cylinder into the anatomy and advancing it to the target location before the cylinder swells to its required therapeutic size.

23. An apparatus as described in claim 1, further comprising:
a protrusion extendable from the distal end of said delivery device, said protrusion being contained within said sheath; said protrusion being extendable toward the distal end of said sheath so as to puncture the sealed distal end of said sheath and cause it to open; and wherein the delivery device is configured to enable relative movement of the sheath and the foam cylinder so as to enable drawing the sheath proximally and pushing said foam cylinder through the open distal end of said sheath within the patient's anatomy.

24. An apparatus as described in claim 3, wherein the coating comprises an antithrombogenic material, and wherein said anti-thrombogenic material is selected from the group consisting of heparin and a hydrophillic material.

25. An apparatus as described in claim 3, wherein the coating comprises a permeable anti-thrombogenic membrane, and the anti-thrombogenic membrane comprises a membrane material selected from the group consisting of: a hydrophillic polymer film, a micro-porous film, and a polymer film with laser-cut holes.

26. Apparatus as described in claim 1, further comprising means for preventing the medicament from entering the flow of the patient's bodily fluids.

27. Apparatus as described in claim 26, wherein the means for preventing the medicament from entering the flow of the patient's bodily fluids comprises an impermeable membrane covering at least the central lumen and the end surfaces of the foam cylinder, so as to prevent the medicament from leaking from the foam cylinder.

28. Apparatus as described in claim 27, wherein the portion of said impermeable membrane which covers the end surfaces of the foam cylinder extends onto and covers a portion of the outer surface of said cylinder near each end surface.

29. An apparatus as described in claim 1, further comprising an inner support means disposed within the central lumen of the compressed foam cylinder, configured so as to provide cylindrical support to the cylinder when in its expanded state.

30. An apparatus as described in claim 29 wherein said inner support means is selected from the group consisting of: a resilient skin covering at least the central lumen and the end surfaces of the foam cylinder; a helical coil of superelastic ribbon which expands when the foam cylinder is allowed to expand; and, at least one resilient serpentine coil which expands when the foam cylinder is allowed to expand.

31. Apparatus as described in claim 29 wherein the inner support means is configured to be pulled into a lumen formed in the delivery device for removal from the patient.

32. Apparatus as described in claim 30, wherein said inner support means comprises a plurality of serpentine coils.

33. An apparatus as described in claim 32 wherein the serpentine coils are configured to be pulled into a lumen formed in the delivery device for removal from the patient.

34. Apparatus as described in claim 1 wherein the delivery device comprises a catheter having at least one openable mouth at its distal end, into which the foam cylinder may be retracted for removal from the patient following use.

35. Apparatus as described in claim 1 wherein the end surfaces of the compressed foam cylinder comprise resilient lips configured to provide a seal between the end surfaces of the foam cylinder and a body lumen.

36. An apparatus as described in claim 35 wherein said lips are selected from the group consisting of: convoluted conical lips; cylindrical lips; petal shaped lips; and lips configured to swell by absorbing fluid.

37. An apparatus as described in claim 35, wherein said lips are spring-loaded.

38. Apparatus as described in claim 35, further comprising a hydrophilic gel disposed over the outer surface of said resilient lips so as to enhance said seal.

39. An apparatus as described in claim 1, further comprising a hydrophillic gel perfused into portions of the foam cylinder adjacent said central lumen and said ends, residing in cells of the foam material and configured to occlude the foam cells when hydrated.

40. An apparatus for selectively delivering a medicament to a target location in a body lumen, comprising:

a hollow cylinder of a fluid-permeable, resilient material, said cylinder having an outer surface, a central lumen, and proximal and distal ends, said cylinder defining proximal and distal openings of the central lumen, said cylinder being initially held in a compressed configuration by means of a sheath disposed thereabout, the permeable cylinder being formed of a material which is expandable when in contact with a bodily fluid;

a delivery device configured for introducing the compressed cylinder into the body lumen, said delivery device having a proximal end and a distal end, said compressed cylinder being carried by the delivery device adjacent the distal end of said delivery device, whereby the compressed cylinder may be advanced into a patient's anatomy and placed adjacent to the target location;

means for breaking the seal and removing the sheath from about the cylinder, thereby allowing the cylinder to expand within the body cavity when it has been placed adjacent to the target location, so as to facilitate contact of the walls of the body cavity with the outer surface of said foam cylinder, and allowing the patient's bodily fluids to flow through the body lumen past the cylinder via the central lumen of said cylinder;

means for providing a medicament to the form cylinder such that the medicament is placed in contact with said walls; and means for inhibiting passage of the medicament into the lumen.

41. A method for facilitating selectively delivering a medicament to a target location of a wall of a body lumen, comprising the steps of:

a) providing an apparatus comprising:

a compressed hollow cylinder of permeable, expandable material, said cylinder having an outer surface, a central lumen, and proximal and distal ends defining openings in an expanded state, the cylinder being configured to facilitate fluid flow through the body lumen past the cylinder in an expanded state in a body lumen via the central lumen;

a delivery device configured for introducing the compressed cylinder into a patient's body lumen, said delivery device having a proximal end and a distal end, said compressed cylinder being carried near the distal end of said delivery device, whereby the compressed cylinder may be placed adjacent to the target location;

means for expanding the cylinder within the body cavity when it has been placed adjacent to the target location so as to contact the walls of the body cavity with the outer surface of said foam cylinder, allowing the patient's bodily fluids to freely flow through the central lumen of said cylinder;

means for perfusing said cylinder with a medicament comprising at least one hollow tube extending at least the length of the delivery device, said at least one tube having a first end which extends outside the patient and is configured to receive a medicament, and a second end adjacent the foam material, whereby medicament may be selectively introduced into said first end and thereby flow from said second end into the foam material, thereby placing the medicament in contact with said walls;

means for inhibiting the medicament from entering a flow of the patient's bodily fluids in the body lumen;

b) introducing said apparatus into the anatomy of the patient;

c) directing said apparatus to an anatomical location in need of medicament;

d) expanding the cylinder within the patient so as to contact the walls of the body cavity with the outer surface of said foam cylinder, while allowing the patient's bodily fluids to freely flow through the central lumen of said cylinder;

e) delivering a medicament to the target location by introducing the medicament into the first end of the hollow tube, such that the medicament flows out of the second end of said tube into the foam material, and is held in contact with the walls of the patient's body cavity for sufficient time to be absorbed thereby.

42. The method of claim 41 further comprising the step of coating said cylinder with an anti-thrombogenic agent before introducing said apparatus into the anatomy of the patient.

43. The method of claim 41 wherein the step of expanding said cylinder within the patient further comprises the step of removing a sheath which surrounds the compressed cylinder, so as to allow the cylinder to expand within the patient's anatomy.

44. The method of claim 41 wherein the step of expanding said cylinder within the patient further comprises the step of allowing the cylinder to swell when contacted by bodily fluids.

45. The method of claim 41 wherein the step of removing the apparatus from the patient's anatomy following use further comprises retracting said cylinder into the lumen of a catheter having an openable mouth in the distal end thereof.

46. The method of claim 41 wherein the step of removing the apparatus from the patient's anatomy following use further comprises capturing said apparatus with a capturing device disposed at the distal end of the delivery device.

47. A method of manufacturing an apparatus for selectively delivering a medicament to a target location of a wall of a patient's body cavity, comprising the steps of:

a) forming a hollow cylinder of permeable, expandable foam, said cylinder having an outer surface, a central lumen, and proximal and distal ends;

b) forming an outer skin layer on at least the central lumen of said cylinder, configured for inhibiting the medicament from entering a flow of the patient's bodily fluids in the body cavity;

c) attaching the cylinder to the distal end of a delivery device configured for introducing the compressed cylinder into the patient's body lumen, said delivery device having a proximal end and a distal end, so that the foam cylinder may be advanced into a patient's anatomy and placed adjacent to the target location by advancing the delivery device into the patient's anatomy;

d) attaching to the cylinder a means for providing a medicament to the foam cylinder such that the medicament may be perfused into said foam material;

e) forming a sheath about the outer surface of said cylinder, whereby the foam cylinder is tightly compressed upon the distal end of said delivery device, and sealed from external contact; and f) forming means for breaking the seal and removing the sheath from about the cylinder, thereby allowing the cylinder to expand within the body cavity so as to contact the walls of said cavity with the outer surface of said foam cylinder at the target location, allowing the medicament to be absorbed by the wall of the patient's body cavity, while at the same time allowing the patient's bodily fluids to freely flow through the central lumen of said cylinder.

48. The method of claim 47 wherein the step of forming a skin on at least the central lumen and end surfaces of said cylinder comprises the step of forming said cylinder by infecting foam into a mold such that the foam forms a skin on all surfaces in direct contact with the mold.

49. The method of claim 47 wherein the step of forming a skin on at least the central lumen and end surfaces of said cylinder comprises the steps of:

m) forming said cylinder by means of extruding a foam material with a skin on the inside surface of the central lumen; and n) coating the end surfaces of the cylinder with a hydrophillic gel which occludes the foam cells when hydrated.

50. The method of claim 47 wherein the step of forming a skin on at least the central lumen and end surfaces of said cylinder comprises the steps of:

o) forming said cylinder by means of extruding a foam material with a skin on the inside surface of the central lumen; and p) coating the end surfaces of the cylinder with material a form a skin.

51. The method of claim 47 wherein the step of forming a skin on at least the central lumen and end surfaces of said cylinder comprises the steps of:

q) forming a foam cylinder without a skin; and r) bonding a skin onto the surface of said foam cylinder.

52. The method of claim 51 wherein the step of bonding a skin onto the surface of said foam cylinder comprises the step of dipping said cylinder so as to coat selected surfaces with a liquid material which cures and becomes a skin.

53. The method of claim 51 wherein the step of bonding a skin onto the surface of said foam cylinder comprises the step of dipping a cylindrically shaped skin material into a liquid foam material to thereby form the foam cylinder upon the preformed skin.

54. The method of claim 51 wherein the step of bonding a skin onto the surface of said foam cylinder comprises the step of spraying a skin forming material upon the surface of the cylinder.

55. The method of claim 54, further comprising the steps of:

s) inverting the foam cylinder before spraying the skin forming material thereon so as a expose the central lumen portion of the cylinder; and t) re-inverting said cylinder following application of the skin so that the skin coated portion resumes its position as the surface of the central lumen of the cylinder.

56. The method of claim 47, further comprising the step of providing the ends of the cylinder with conical lips configured to facilitate a seal between the end surfaces of the foam cylinder and the body lumen.

57. The method of claim 47, further comprising the step of providing the ends of the cylinder with elastic lips so as to facilitate a seal between the end surfaces of the foam cylinder and the body lumen.

58. The method of claim 47, further comprising the step of providing the ends of the cylinder with a plurality of petal-shaped lips configured so as to facilitate a seal between the end surfaces of the foam cylinder and the body lumen.

59. The method of claim 47, further comprising the step of coating the ends of the foam cylinder with a hydrophillic gel which occludes the foam cells when hydrated so as to facilitate a seal between the end surfaces of the foam cylinder and the body cavity.

* * * * *